United States Patent [19]

Trafford

[11] Patent Number: 5,685,763

[45] Date of Patent: Nov. 11, 1997

[54] STRIPPING METHOD FOR LEAF CUTTER BEE NEST BLOCK

[76] Inventor: Norman F. Trafford, General Delivery, Garland, Manitoba, Canada, R0L 0W0

[21] Appl. No.: 517,621

[22] Filed: Aug. 22, 1995

[51] Int. Cl.$^6$ ............................................. A01K 51/00
[52] U.S. Cl. ................................................. 449/56
[58] Field of Search ................................. 449/1, 4, 56

[56] References Cited

U.S. PATENT DOCUMENTS 3,889,306  6/1975  Geertson ............................ 449/56
4,293,966  10/1981  Weiderrich ........................ 449/1
5,149,292  9/1992  Eggerman ...................... 449/56 X Primary Examiner—Robert P. Swiatek
Attorney, Agent, or Firm—Robert W. B. Bailey

[57] ABSTRACT

A method of stripping leaf cutter bee nest blocks passes several sets of stripping pins through the block in a single pass. Each set of pins has a different length, the lengths differ so that only one set of pins at a time contacts the seal plugs in the nest block tunnels. One set of pins contacts the plugs and breaks them loose before next set contacts the plugs. The pins are spaced so that each pin of a set is not directly adjacent a pin of an immediately preceding or succeeding set. The method increases speed and reduces cocoon crush.

17 Claims, 2 Drawing Sheets

STRIPPING METHOD FOR LEAF CUTTER BEE NEST BLOCK

This invention concerns a method of stripping leaf cutter bee cocoons from leaf cutter bee nest blocks, such as those described in U.S. Pat. No. 5,403,226, issued Apr. 4, 1995, to applicant, herein incorporated by reference.

Although the invention is described and referred to specifically as it relates to specific methods of stripping leaf cutter bee nests, it will be understood that the principles of this invention are equally applicable to similar methods and accordingly, it will be understood that the invention is not limited to such methods.

BACKGROUND OF INVENTION

Leaf cutter bees are increasingly valuable in crop pollination. In contrast to honey bees, which fly long distances (several miles) and pollinate over wide areas, leaf cutter bees fly short distances (several hundred yards) and pollinate within a small area.

The continued advance of the Africanized "killer" bee, reaching Texas in 1993, and other unrelated honey bee disease problems, has raised potential long term concerns with honey bee pollination. Leaf cutter bees have become attractive potentially competitive alternative pollinators.

Accordingly leaf cutter bee pollination has generated and continues to generate substantial interest. Leaf cutter bees are solitary bees, unlike honey bees where only one female bee, the queen, lays fertile eggs, every female leaf cutter bee lays fertile eggs. The life cycle is quite different, the leaf cutter bees, female and male, overwinter as cocoons (pupae), emerging in the spring. The males who outnumber the females about two to one, mate with the females after emergence. The females then cut leaves and prepare cells in which they lay their eggs, which hatch into grubs, then become overwintering pupae or cocoons. The female typically prepares from ten to twenty-five egg cells, each with their cut leaf, which develop into cocoons (pupae), and later bees, of which about a third are female.

Nests are provided having in them tunnels or bores to accommodate the cocoons, typically about 3 to 4 inches deep.

If the cocoons are allowed to incubate in the nests, parasites, predators and disease cannot be controlled and there is some cocoon loss from the heat generated by incubation. It is therefore preferable to strip the cocoons from the nests. One sort of nest has blind, one ended tunnels, and cannot be stripped. Another is composed of laminates having half tunnel grooves on each face, these can be stripped manually at about half an hour a nest, or automatically at a somewhat faster rate by separating the laminates. More recently the laminates composed of polystyrene, not wood, are stripped as if molded or drilled nest blocks, bound into a block using adhesive tape or like material. These last have drilled or more preferably molded holes extending through a nest block. These may be stripped by stripping machines, currently available technology strips by passing rods or pins through the tunnels or holes in the blocks, which break loose the outer seal plug or cap composed of leaves typically about ½ inch thick. There are various forms of stripper currently available. One form has an outer cutting tube circumferential to the hole, and an inner pushing rod, another a pushing rod. Various arrangements can be used, but at present only one, two or at most three rows of holes are stripped at a time. The hole rows are typically 30 with a central gap, so at most 90 holes are stripped at a time, which means the machine must make at least 17 or so stripping passes to clear a normal block with some 1500 or 1600 odd holes, or at least 40 passes to strip one of the 3600 odd holes of the nest block of U.S. Pat. No. 5,403,226 noted above. All the holes cannot be simultaneously stripped because of the pressure exerted to break the seal loose would damage the nest blocks.

The time and labor consumed in stripping the nest blocks are considerable, the fastest current stripping machines strip about 60 nests per hour, and the proportion of cocoons crushed is considerable, 5% being regarded as reasonable. Crushed cocoons do not incubate. The alternative of not stripping does not control disease, parasites, and predators, or losses during incubation.

Therefore it is desirable to introduce a more effective method of stripping cocoons from nest blocks.

PRIOR ART

No closely relevant prior art is known to applicant.

It is a principal object of the invention to provide a method capable of stripping as much as possible an entire leaf cutter bee nest block in a single operation. It is a subsidiary object of the invention to provide a method capable of stripping an entire nest block in a single operation. It is a further principal object of the invention to provide a method capable of stripping a nest block causing minimal damage to the block. It is a further principal object of the invention to provide a method of stripping a nest block causing minimal damage to the cocoons therein. It is a further principal object of the invention to provide a fast, efficient, and labor saving method of stripping leaf cutter bee nest blocks.

DESCRIPTION OF THE INVENTION

The invention envisages use of apparati to carry out the method. The apparatus as described specifically herein is not contemplated as the sole possible apparatus usable in the inventive process, as those skilled in the art will be aware a number of widely different arrangements can be made to carry out the same functions.

The apparatus contemplated for the method comprises an array of pins, each of which corresponds when in aligned position to a hole or tunnel in a leaf cutter bee nest block. These pins are typically mounted in a horizontal plate or plates which may be raised and lowered vertically as an integral unit. Advisably positioning pins are provided to locate the nest block so that its holes are precisely aligned with the pins. The pins are about 0.205 inch diameter, say approximately 13/64 inch, while the holes are about 15/64 inch diameter expanding to about ¼ inch in the blocks, of U.S. Pat. No. 5,403,226. The pins should not be much larger in diameter, but may be somewhat smaller as 3/16 inch is known to work with a drill bit. All nest blocks have half tunnels or holes on the end, which may serve to locate the block exactly, in cooperation with the positioning pins. These half holes or tunnels join with those in the next block in standard stripping machines, so that the advancing mechanism of the standard stripping machines passes the nest blocks through continuously, without this row of pseudo holes between successive blocks the striping machine would have to be stopped for each block. The location of the locating pins and the stripping pins is however merely a matter of precision engineering, as those skilled in the art will appreciate, as long as the holes have specific dimensions and form a specific pattern, it is a relatively simple matter to provide an array of pins, where each pin corresponds exactly to a given nest block hole, while the skills to provide this are not that common, they are most certainly available. The plate or plates must be lowered precisely parallel to the nest block, again a matter of precision engineering while the support under the block must not block any of the holes, so the cocoons fall into a receptacle, which max be a tray or other receiving device. The holes are envisaged as in typical nest blocks as consisting of a series of rows of thirty holes divided into two groups of fifteen separated by a central space. Support plates or members are provided at the edges and optionally support is provided under the central space. A support having holes therein corresponding to the pins and nest block holes may optionally be present, The chamber in which the nest block is stripped has about 1/16 inch tolerance of movement, which allows the block to be moved in and engage the locating pins, of which there are two sets each containing a plurality of pins, 6 or 8 being convenient, although the number can be varied as those skilled in the art would appreciate. The chamber itself is adjustable in size, and may be varied in size to fit runs of various types of nest block. To fit the machine the nest blocks in a run must be all exactly the same size within the 1/16 inch tolerance.

The device however is designed to apply the method, not the other way round.

The method requires that all holes be stripped in a single operation, and that the pressure be applied in such fashion as not to damage the nest block. This is especially important considering that the nest block is supported only at its edges and optionally along the middle, unless an apertured support is incorporated in the design.

When the nest block of U.S. Pat. No. 5,403,226 is stripped, since the holes increase in size from the seal as soon as the seal is broken away from the walls minimal pressure should be required, to strip the cocoons from the block. This was tested using a 3/16 inch drill, it was found while some force was required to dislodge the seal, thereafter the weight of the drill bit alone was enough to strip the cocoons from the hole. That is once the seal was broken away from the walls of the hole, minimal pressure was needed, in most cases. Thus the entire pressure applied is to break away the seal from the hole walls, in most cases. Sometimes some or all cocoons are attached to the tunnel or hole wall, or fit more tightly, and here some residual force may be required to break them away from the hole wall.

The seals are approximately ½ inch thick at most, so to dislodge a seal would take at most ½ inch of travel by a dislodging pin, in fact about ¼ inch of travel will break most if not all seals loose. It was therefore decided to apply equal numbers of pins at predetermined intervals spaced about ¼ inch vertically apart, in groups. As the pins have a predetermined array, corresponding to the nest block holes, the pins must form groups of pins having a plurality of differing lengths projecting downward from the plate. The number of groups of pins of equal length, and their consequent horizontally spaced arrangement required determination. To avoid undue block stress and strain it was decided that the pins of adjacent lengths (differing by about ¼ inch in length) should not be adjacent, i.e. they should not be aligned either from row to row, or within rows, at approximately 0.4 (2/5) inches distance, but at least diagonally spaced, say 0.57 inches apart. Any pin array must be repeating and since a 2×2 arrangement must contain adjacent pins of adjacent lengths, this will require a 3×3 repeating pin arrangement, as those skilled the art would be aware.

When the pins are labelled in order of length 1 being the shortest and 9 the longest, and the central pin of the repeating array is defined as 9, the arrangement becomes something like the exemplified

```
1 3 7
6 9 4
8 5 2
``` which is identically equivalent to

```
7 3 1      8 5 2      2 5 8
4 9 6      6 9 4      4 9 6
2 5 8      1 3 7      7 3 1
``` all of which are transformations with rows remaining rows, since the inrow hole distance is less than the interrow distance the array is not quite square. If this minor difference is ignored then

```
2 4 7      7 4 2      1 6 8      8 6 1
5 9 3      3 9 5      3 9 5      5 9 3
8 6 1      1 6 8      7 4 2      2 4 7
``` are practically identical, as would he appreciated by those skilled in the art.

While numerous arrays can be constructed with a central 9 and no two pins of adjacent length directly adjacent inrow or interrow, the one first shown

```
1 3 7
6 9 4
8 5 2
``` was in fact utilized, although the others shown are equivalent.

This particular arrangement is preferred, because no two successive pins are directly adjacent each other, but are diagonal, including pins in neighboring arrays. Minor variations are possible without changing the basic principle, the fact that inter-row distance (vertical) is slightly greater than the within-row distance (horizontal) making the array rectangular rather than exactly square has no effect, the diagonal distance is the same. Once the array is defined by the 9 pin, which is the longest, the 8 pin must lie in one of the corners, which is shown as the bottom left, although it can be any corner. The 7 pin is preferably placed in the opposing corner. If it is not but placed in either of the other two positions diagonal to the 8 pin (shown as 3 and 4 in the preferred array) two other sets of arrays of similar properties may be easily generated by those skilled in the art as long as two successive pins of adjacent lengths are diagonal rather than adjacent. Each final array has four exact and four close equivalents, where the practical relationship of the pins to each other is identical. The idea is to spread the pressure as evenly as possible across the nest block as each successive set of pins pushes through the seal in the holes.

In broadest aspect the invention is directed to a method of stripping leaf cutter bee cocoons from a leaf cutter bee nest block having tunnels therein forming a rectangular array. The method comprises the step of passing an array of stripping pins having a plurality of multiple length subarrays, through the nest block tunnels, one pin per tunnel in a single steady pass, subarray of pins after subarray of pins, longest first, shortest last. The pins in each subarray of pins have the same length, so that each subarray of pins in turn contacting seal plugs in the tunnels, breaking the seal plugs away from the tunnels and pushing said plugs and cocoons out of the tunnels. The pin lengths are staggered so that each subarray of pins after the longest contacts the seal plugs after the immediately preceding subarray of pins has broken the seal plugs away from the tunnels. The pins in each subarray after the first pass through a tunnel which is not directly adjacent to a tunnel of the subarray containing a pin of the immediately preceding subarray of pins.

The invention in a broad aspect, is directed to a method of stripping leaf cutter bee cocoons from a leaf cutter bee nest block, which has tunnels forming a rectangular array. The nest block is first positioned with its seal plugs toward an array of stripping pins of multiple lengths so that each nest block tunnel corresponds to one said stripping pin. Typically the nest block has opposed ends, sides and surfaces, with the tunnels containing cocoons and seal plugs with the seal plugs abutting one such surface. The bees form the plugs in the tunnels substantially flush with the surface. Half tunnels or recesses are present in the ends of the block as noted earlier. Preferably the nest block is dried before it is stripped, which reduces the tendency of the nest to be damaged, the nests may be dry anyway, but it is preferred to dry them to make sure. Preferably the nest block is first placed on support means, with its seal plugs uppermost, more preferably over receptacle means to receive cocoons and seal plugs. Preferably the nest block is positioned on the support means by engaging the tunnels in the nest block with positioning pins. These pins are conveniently attached to the same plate as the stripping pins. When positioned the block is opposed to an array of stripping pins of multiple lengths so that each nest block tunnel corresponds to one stripping pin. Preferably the block lies horizontally beneath the vertical pin array.

The stripping pins of a particular length form a distinct subarray of pins, the array consisting of a plurality of said subarrays, preferably nine such subarrays. More preferably the subarrays lengthen by the same distance. Each distinct subarray of pins corresponds to a distinct subarray of tunnels.

The array of stripping pins then passes through the nest block tunnels in a single steady pass, subarray of pins after subarray of pins, longest first, shortest last. The pass must be steady to break all the seal plugs in turn, and slow enough to push out the cocoons without damage, it must also be fast enough to be viable. In this process each subarray of pins in turn contacts said seal plugs, then breaks the seal plugs away from the tunnels and pushes the plugs and cocoons out of the tunnels, preferably into receptacle means provided to receive them.

Each subarray of pins after the first contacts its corresponding seal plugs after the immediately preceding subarray of pins has broken its corresponding seal plugs away from the tunnels. This is basic to the method, that is only some of the pins exert the maximum force at a time, which is that applied to break the seals loose. This is achieved by only having a proportion of the pins doing so at each time.

Each pin in each subarray after the first passes through a tunnel which is not directly adjacent to a tunnel of the subarray containing a pin of the immediately preceding subarray of pins. That is it is not in adjacent in the same row or column to a pin of the immediately preceding subarray. This is also basic to the invention as the strain due to the force applied to break the seals loose, must not be concentrated but dispersed or distributed to avoid damaging the nest. Preferably each pin in each subarray is diagonally adjacent to a pin of the immediately preceding subarray. The increased distance, by approximately the square root of two, is effective to prevent damage should both pins be exerting pressure at the same time. Although the method envisages that the seals are broken loose by a preceding subarray of pins, before the succeeding subarray contacts its seals, this is not always the case, and damage can result with directly adjacent pins. Ideally and conveniently the subarrays of pins each comprise substantially the same number of pins, and more preferably exactly the same number.

Preferably the array of stripping pins are withdrawn from the block. Preferably the positioning pins are disengaged from the block. Preferably the block is then removed from its support means.

Use of the machine demonstrated that the method was most efficient, damage to the blocks was negligible, crushed cocoons were about 1.5% as certified by the Leaf Cutter Bee Cocoon Testing Station, a significant improvement over about 5% crushed cocoons taken as a general optimum. Finally the stripping speed was gratifyingly fast with manual handling, 2 nests per minute, which with automatic feed equipment can obviously be substantially increased. The fact that manual handling on the new machine is twice as fast as automatic handling on current stripping machines, and that the nest blocks stripped were almost twice the usual size, was felt to constitute a significant improvement over the prior art.

Careful examination of the crushed cocoons suggests that crushing occurred only when the seal was absent, this happens when the bee dies before completing a full tunnel or hole and does not seal the cocoons, that is the degree of crush of sealed holes was probably negligible.

DESCRIPTION OF STRIPPING MACHINE AS USED IN THE INVENTION

Numeral 11 denotes the repeating pin unit as used in a stripping machine used in the inventive process. This comprises horizontal plate 10, which has protruding downward pins 1 to 9 numbered in order of length, 1 being the shortest and 9 the longest, the arrangement being

| | | |
|---|---|---|
| 1 | 3 | 7 |
| 6 | 9 | 4 |
| 8 | 5 | 2 |

Figure 1:
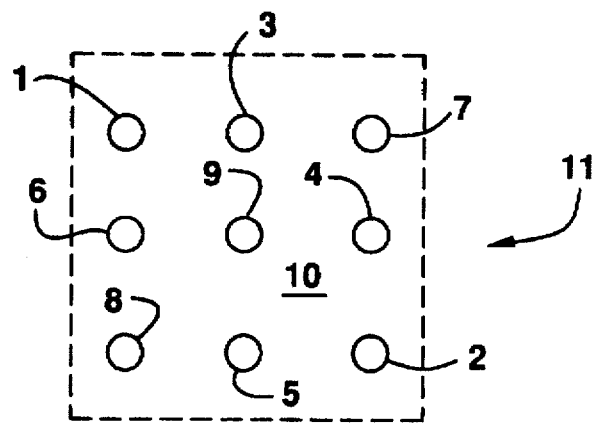
FIG. 1 shows a bottom plan view of a pin array element of a stripping machine used in the inventive process.
Figure 2:
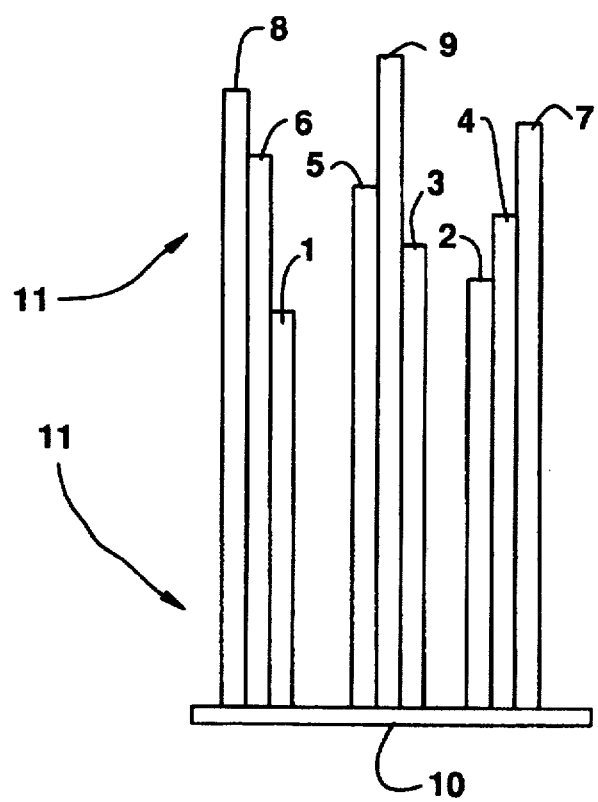
FIG. 2 shows a slightly angled side view of the element of FIG. 1 from the bottom as portrayed in FIG. 1.
Figure 3:
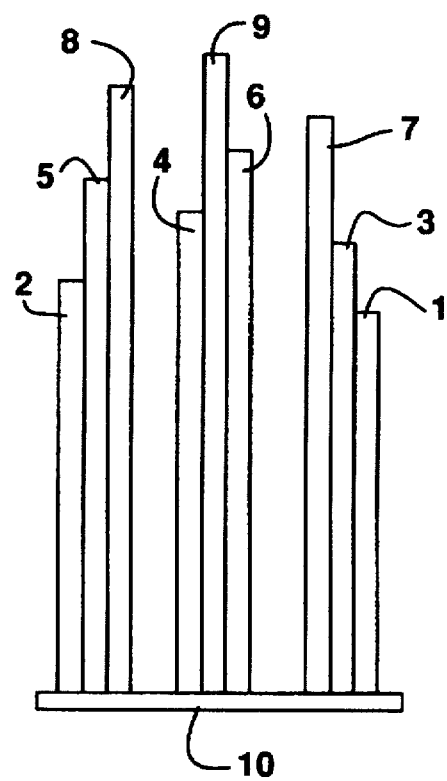
FIG. 3 shows a slightly angled side of the element of FIG. 1 from the righthand side as portrayed in FIG. 1.
Figure 4:
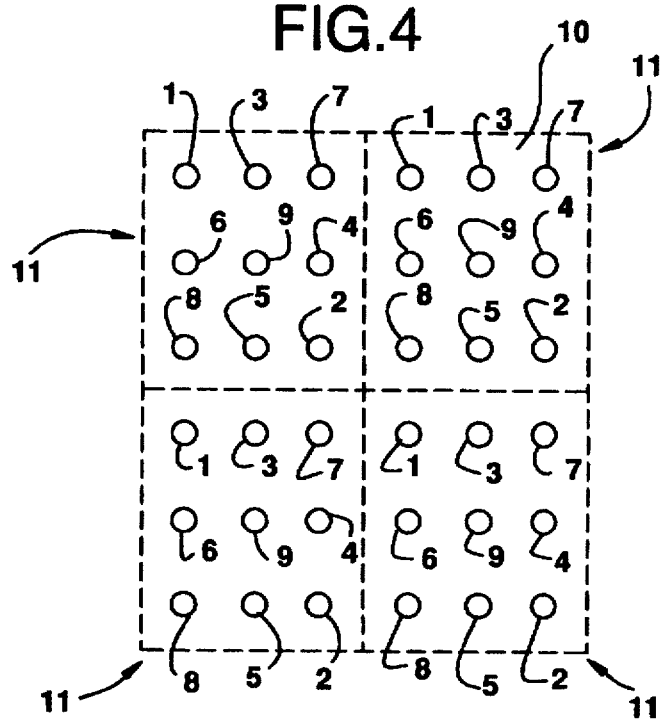
FIG. 4 shows a bottom plan view of four adjacent pin array elements of FIG. 1 in a stripping machine used in the inventive process.
Figure 5:
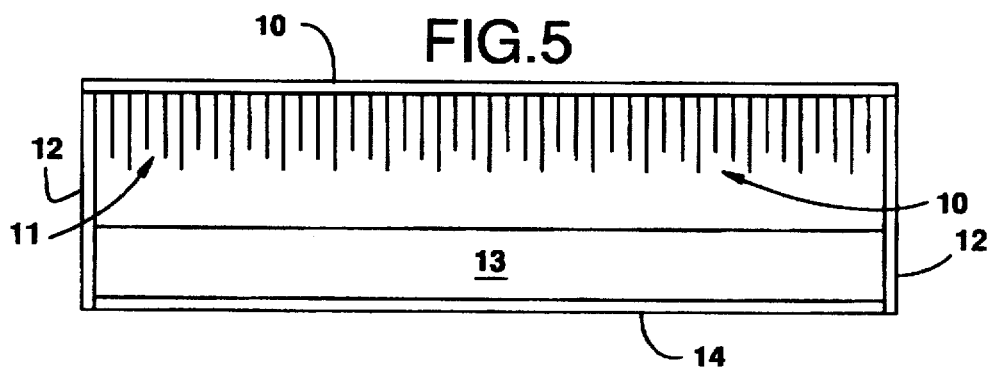
FIG. 5 shows a side view of a stripping machine used in the inventive process.
Figure 6:
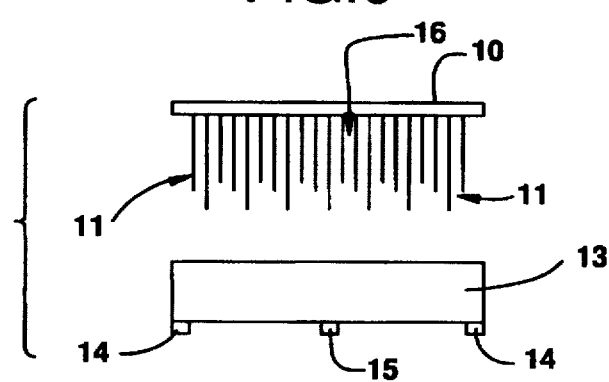
FIG. 6 shows a part sectional end view of a stripping machine used in the inventive process.

FIG. 1 shows element 11 looking upward at plate 10. FIG. 2 shows a side view from the bottom of FIG. 1 as drawn, the lefthand vertical row pins 8, 6 and 1 are show on the left, the central vertical row pins 5, 9 and 3 in the middle, and the righthand vertical row pins 2, 4 and 7 on the right. In FIG. 3 the view is from the righthand side of FIG. 1, the bottom horizontal row pins 8, 5, and 2 are shown on the left, the central horizontal row pins 4, 9 and 6 in the middle and the top horizontal row pins 1, 3 and 7 on the right. In FIG. 4 are shown four adjacent pin elements 11 as they are on plate 10. Pin 1 is long enough to pass cleanly through the nest block, which is typically some 3 to 4 inches thick, the other pins are longer by, incremental steps of about ¼ inch each. FIG. 5 shows nest block 13 held in place by vertical positioning pins 12, plate 10 has downward pin elements 11, side support 14 supports nest block 13. In FIG. 6 the positioning of side supports 14, outside the pin elements 11 and optional central support 15 is shown inside the pin elements 11 corresponding central gap 16 in the pin elements 11 of plate 10.

As those skilled in the art would realize these preferred described details and processes can be subjected to substantial variation, modification, change, alteration, and substitution without affecting or modifying the function of the described embodiments. Although embodiments of the invention have been described above, it is not limited thereto, and it will be apparent to persons skilled in the art that numerous modifications and variations form part of the present invention insofar as they do not depart from the spirit, nature and scope of the claimed and described invention.

I claim:

1. A method of stripping leaf cutter bee cocoons from a leaf cutter bee nest block having tunnels therein forming a rectangular array comprising the step of passing an array of stripping pins having a plurality of multiple length subarrays, pins in each subarray of pins having the same length, through said nest block tunnels, one pin per tunnel in a single steady pass, subarray of pins after subarray of pins, the first subarray to enter said nest block tunnels comprising the longest pins, the last subarray to enter said nest block tunnels comprising the shortest pins each said subarray of pins in turn contacting seal plugs in said tunnels, breaking said seal plugs away from said tunnels and pushing said plugs and cocoons out of said tunnels each said subarray of pins after the longest contacting said seal plugs after the immediately preceding subarray of pins has broken said seal plugs away from the tunnels each said pin in each said subarray after the first passing through a tunnel which is not directly adjacent to a tunnel containing a pin of the immediately preceding subarray of pins.

2. A method of claim 1 comprising the steps of positioning said nest block with its seal plugs toward an array of stripping pins of multiple lengths so that each nest block tunnel corresponds to one stripping pin said stripping pins of a particular length forming a distinct subarray of pins, said array consisting of a plurality of distinct subarrays of pins each distinct subarray of pins corresponding to a distinct subarray of tunnels.

3. The method of claim 2, additionally comprising the preceding step of drying said nest block.

4. The method of claim 3, wherein said nest block is positioned by positioning pins engaging half tunnels in said nest block.

5. The method of claim 2, wherein said nest block is positioned by positioning pins engaging half tunnels in said nest block.

6. The method of claim 2, additionally comprising receiving said cocoons and seal plugs in a receptacle therefor.

7. A method of claim 2, wherein each said subarray of pins comprises substantially the same number of pins.

8. A method of stripping leaf cutter bee cocoons from a leaf cutter bee nest block having opposed ends, sides and surfaces, said surfaces having tunnels therein forming a rectangular array said tunnels containing cocoons and seal plugs abutting one said surface, said ends having therein recesses forming half tunnels, comprising the steps of drying said nest block placing said nest block on support means above receptacle means with said seal plugs uppermost positioning said nest block on said support means by engaging said half tunnels in said nest block with positioning pins, beneath an array of stripping pins of multiple lengths so that each nest block tunnel corresponds to one said stripping pin said stripping pins of a particular length forming a distinct subarray of pins, said array consisting of a plurality of subarrays each distinct subarray of pins corresponding to a distinct subarray of tunnels passing said array of stripping pins through said nest block tunnels in a single steady pass, subarray of pins after subarray of pins, the first subarray to enter said nest block tunnels comprising the longest pins, the last subarray to enter said nest block tunnels comprising the shortest pins each said subarray of pins in turn contacting said seal plugs, breaking said seal plugs away from said tunnels and pushing said plugs and cocoons out of said tunnels each said subarray of pins after the first contacting said seal plugs after the immediately preceding subarray of pins has broken said seal plugs away from said tunnels each said pin in each said subarray after the first passing through a tunnel which is diagonally adjacent to a tunnel containing a pin of the immediately preceding subarray of pins collecting said cocoons and said seal plugs in said receptacle means.

9. The method of claim 8 comprising the additional subsequent step of withdrawing said array of stripping pins from said block.

10. The method of claim 9 comprising the additional subsequent step of disengaging said positioning pins from said block.

11. The method of claim 10 comprising the additional subsequent step of removing said block from said support means.

12. A method of claim 8, wherein each said subarray of pins comprises substantially the same number of pins.

13. A method of stripping leaf cutter bee cocoons from a leaf cutter bee nest block having opposed ends, sides and surfaces, said surfaces having tunnels therein forming a rectangular array said tunnels containing cocoons and seal plugs abutting one said surface, said ends having therein recesses forming half tunnels, comprising the steps of drying said nest block placing said nest block on support means above receptacle means with said seal plugs uppermost positioning said nest block on said support means by engaging said half tunnels in said nest block with positioning pins, beneath an array of stripping pins of multiple lengths so that each nest block tunnel corresponds to one said stripping pin said stripping pins of a particular length forming a distinct subarray of pins, said array consisting of nine subarrays each distinct subarray of pins corresponding to a distinct subarray of tunnels passing said array of stripping pins through said nest block tunnels in a single steady pass, subarray of pins after subarray of pins, the first subarray to enter said nest block tunnels comprising the longest pins, the ninth subarray to enter said nest block tunnels comprising the shortest pins each said subarray of pins in turn contacting said seal plugs, breaking said seal plugs away from said tunnels and pushing said plugs and cocoons out of said tunnels said second and subsequent subarrays of pins contacting said seal plugs after the immediately preceding subarray of pins has broken said seal plugs away from the tunnels each said pin in said second and subsequent subarrays passing through a tunnel which is diagonally adjacent to a tunnel containing a pin of the immediately preceding subarray of pins collecting said cocoons and said seal plugs in said receptacle means.

14. The method of claim 15 comprising the additional subsequent step of withdrawing said array of stripping pins from said block.

15. The method of claim 14 comprising the additional subsequent step of disengaging said positioning pins from said block.

16. The method of claim 15 comprising the additional subsequent step of removing said block from said support means.

17. A method of claim 13, wherein each said subarray of pins comprises substantially the same number of pins.

* * * * *